United States Patent
Chao

(10) Patent No.: US 8,382,692 B1
(45) Date of Patent: Feb. 26, 2013

(54) NECK AND SPINE SUPPORT DEVICE FOR A NECK IN FLEXION

(76) Inventor: John Chao, Los Angeles, CA (US)

( * ) Notice: Subject to any disclaimer, the term of this patent is extended or adjusted under 35 U.S.C. 154(b) by 117 days.

(21) Appl. No.: 12/813,219

(22) Filed: Jun. 10, 2010

(51) Int. Cl.
- A61G 15/00 (2006.01)
- A61F 5/37 (2006.01)
- A61F 5/56 (2006.01)
- A61F 5/02 (2006.01)
- A61F 5/00 (2006.01)
- A41D 27/26 (2006.01)
- A47C 20/00 (2006.01)
- A47C 17/86 (2006.01)

(52) U.S. Cl. .............. 602/18; 602/5; 602/12; 602/16; 602/19; 602/32; 602/17; 2/45; 2/468; 128/845; 128/846; 128/848; 5/630; 5/632; 5/636; 5/637; 5/640; 5/648; 5/652; 5/655.9

(58) Field of Classification Search ............ 602/18, 602/5, 12, 16, 19, 32, 17, 902; 2/45, 468, 2/171, 456, 171.2, 69, 207, 208.7, 209.13, 2/209.14, 202–205; 5/636, 637, 640, 630, 5/643, 648, 652, 419, 655.9; 24/265 AC, 24/265 R, 662, 630, 686, 265 BC; 128/845, 128/846, 848, DIG. 23

See application file for complete search history.

(56) References Cited

U.S. PATENT DOCUMENTS

| | | |
|---|---|---|
| 3,964,474 A | 6/1976 | Fox |
| 4,204,529 A | 5/1980 | Cochrane |
| 4,232,663 A | 11/1980 | Newton |
| 4,520,801 A | 6/1985 | Lerman |
| 4,617,691 A | 10/1986 | Monti |
| 4,712,540 A | 12/1987 | Tucker |
| 5,029,577 A | 7/1991 | Sarkozi |
| 5,097,824 A | 3/1992 | Garth |
| 5,116,359 A | 5/1992 | Moore |
| 5,303,890 A | 4/1994 | Carruth |
| 5,320,640 A | 6/1994 | Riddle |
| 5,336,138 A | 8/1994 | Arjawat |
| 5,575,763 A | 11/1996 | Nagata |
| 5,738,640 A | 4/1998 | Carlson-Orsi |
| 6,231,535 B1 * | 5/2001 | Mainiero et al. ............ 602/18 |
| 6,435,617 B1 * | 8/2002 | McNair .................... 297/397 |
| 6,458,090 B1 | 10/2002 | Walpin |
| 6,551,214 B1 | 4/2003 | Taimela |
| 6,599,257 B2 | 7/2003 | Al-Obaidi |
| 6,692,451 B2 | 2/2004 | Splane, Jr. |
| 7,549,970 B2 * | 6/2009 | Tweardy ................... 602/18 |
| 7,789,843 B2 * | 9/2010 | Ray ........................ 602/18 |
| 7,861,326 B2 * | 1/2011 | Harty ...................... 2/468 |

* cited by examiner

Primary Examiner — Patricia Bianco
Assistant Examiner — Nihir Patel
(74) Attorney, Agent, or Firm — Andrew S. Langsam; Pryor Cashman LLP

(57) ABSTRACT

A spine and neck support device adapted to support the anatomical structures in the cervical and upper thoracic spine when the user's neck is in flexion. A cushion conforms about the user's anatomical neck structures and rests on the upper chest of the user. The cushion has a chin support area that avoids contacting the user's chin when the user's head is in a neutral position and contacts the user's chin when the user's neck is in flexion. When the user's neck is flexed and the user's chin contacts the chin support area, the cushion unloads and supports the user's neck. At least one and preferably two straps are attached to the cushion and secure it to the user. The top is sloped downwards from back to front to maximize the user's downward field of vision. A groove in the posterior surface of the cushion accommodates the user's trachea/esophagus.

18 Claims, 7 Drawing Sheets

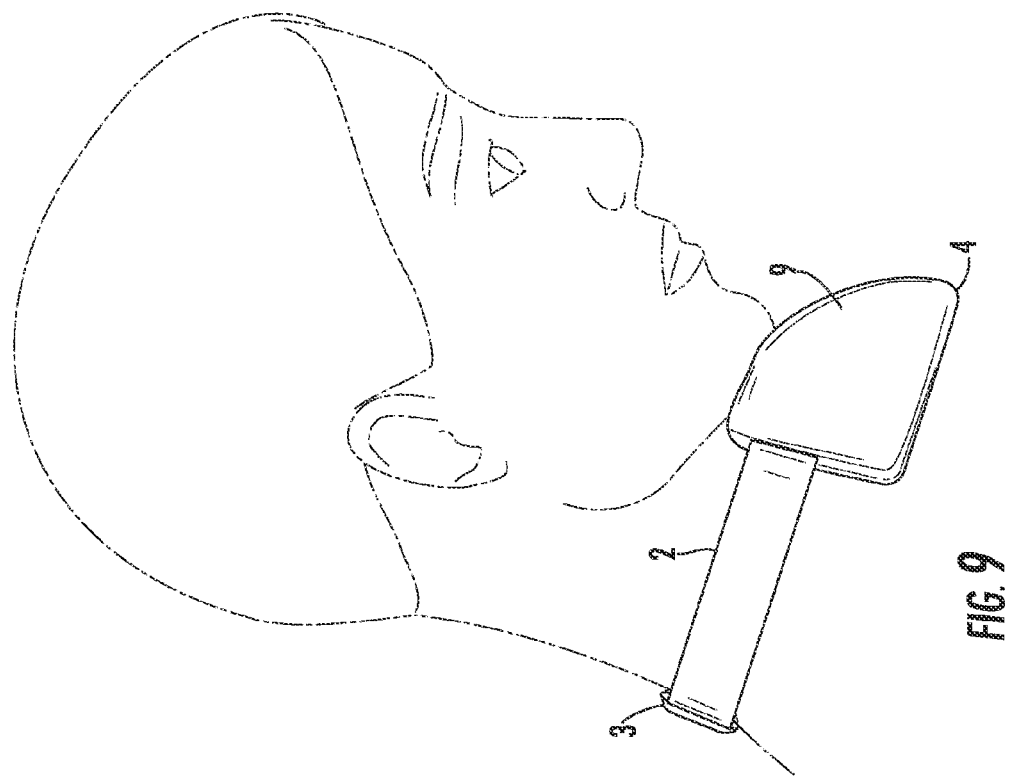
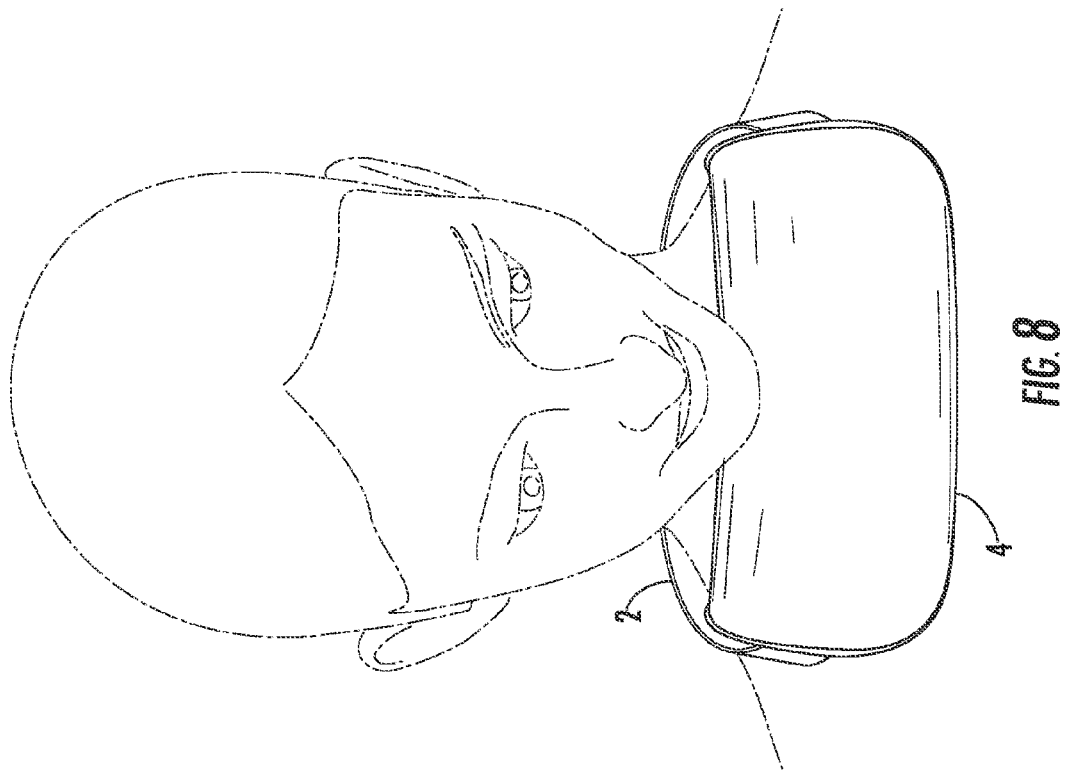

NECK AND SPINE SUPPORT DEVICE FOR A NECK IN FLEXION

BACKGROUND OF THE INVENTION

1. Field of the Invention

The invention relates to the field of orthopedic devices, and more particularly to cervical/head support cushion and therapy devices for the head and neck.

2. Description of Related Art

Many professions require sustained cervical/neck and upper thoracic spinal flexion postures including surgeons, dentists, scientists/researchers looking into microscopes, and students. Many daily activities also require a person to be looking down for an extended period of time such as working at a computer, reading, or writing. The structures (muscles, tendons, ligaments, discs) in the cervical spine and upper thoracic spine are stressed in a sustained flexion in a flexed posture. If one is bending at the waist to look down, the neck could be in a neutral position and those structures not stressed, but that is not a practical way to look down. Also, it would be impossible to hold that position for very long, as it places too much load in the lumbar spine. To look down, it is more practical to flex one's neck, especially for extended periods of time. The upper thoracic spine follows suit with the cervical spine. Safely supporting the head while the neck is in a flexed position is critical in helping to alleviate or even prevent pain and disability, while allowing one to perform their work/activity for a longer period of time. There are many posterior neck muscles that can potentially be affected by extended periods of cervical flexion, including the longissimus capitis, longissimus cervisis, semispinalis capitis, splenius capitis, splenius cervisis, and suboccipital muscles. Excessive time spent in a flexed posture without support can also put excessive forces on the cervico-thoracic interverte-bral discs, ligaments, muscles, tendons, connective tissues, and facet joint, which can lead to pain and/or injury.

Many neck cushions and braces have been made for the purpose of supporting the head and neck while the user/wearer is in a lying down or sitting up position with the head and neck in a neutral position. While they may help to unload the cervical and upper thoracic spine, they do not do so while the user is in a cervical flexion position.

A wide variety of cervical support devices are known and these devices are mostly intended for medical or therapeutic purposes. These devices are typically constructed of rigid or soft materials such as plastic or foam. The device typically rests on the shoulders, supports the neck, and holds the head and neck in a normal eyes- or face-forward anatomical position while the wearer is sitting upright or standing. These devices are not well suited for relatively unrestricted physical activities and typically prevent the user from looking downwards except with only their eyes or having to bend forward from their trunk. Other devices are intended to support the neck and head when the wearer is in a supine or side lying position. These devices are intended to provide support and proper alignment of the head-and-neck during rest or sleep.

One such device is illustrated in U.S. Pat. No. 5,738,640 to Carlson-Orsi. This device includes an upper cervical horizontal cushion, and an attached upper thoracic spine vertical cushion with straps to hold the device against the upper portion of the spine. It is intended to be used in a chair or bed with the wearer's head-and-neck resting against the chair or bed pillow. Again, this device is not intended to be used to provide neck support during physical activities or when the user has to look down. Because of, among other things, the device's top-of-shoulder-straps attachment site onto the cervical (top or horizontal) component of this device's cushions, there is no effective forward pull, and consequently, that device does not and cannot support the head and neck in flexion during downward-looking activities.

The prior art also includes numerous cervical orthoses designed to partially or totally immobilize the head and neck. Examples of such orthoses are described in U.S. Pat. No. 4,204,529 to Crochrane; U.S. Pat. No. 4,520,801 to Lerman; U.S. Pat. No. 4,712,540 to Tucker; U.S. Pat. No. 5,097,824 to Garth; U.S. Pat. No. 5,575,763 to Nagata et al. The immobilization provided by these devices result in a desired spinal alignment, reduced neck muscle strain or spasm and transfers the load of the head to the shoulder area. However, these cervical orthoses create the problem of extended immobilization weakening the muscles that stabilize the head and neck. They do not permit rotation or flexion of the head, therefore limiting the user in the activities in which they can participate. These devices do not allow the user to perform any activities that require cervical/neck flexion, and thus do not and cannot support the head and neck in flexion during downward-looking activities.

Other known cervical therapy devices, such as described in U.S. Pat. No. 5,116,359 to Moore; U.S. Pat. No. 5,320,640 to Riddle et al; U.S. Pat. No. 5,336,138 to Arijawat; U.S. Pat. No. 6,551,214 to Taimela; U.S. Pat. No. 6,599,257 to Al-Obaidi et al; and U.S. Pat. No. 6,692,451 to Splane, support the head and therapeutically exercise the neck in one or more planes. However, these cervical therapy devices are cumbersome cervical therapy devices built onto a chair or table requiring patients to visit a physical therapy facility for cervical therapy and are not portable for use during any desired activities. These devices also do not and cannot support the head and neck in flexion during downward-looking activities.

Another example of the prior art is illustrated in U.S. Pat. No. 6,458,090 to Walpin. The multi-positional support device disclosed allows for support in various fixed degrees of rotation as well as small ranges of head and neck rotation. However, this device presents the problem of allowing only small ranges of head and neck rotation insufficiently exercising atrophied neck muscles to strengthen them to safely support the load of the head and allow extensive ranges of rotation of the head. This device also does not and cannot support the head and neck in flexion during downward-looking activities.

Another example of the prior art is illustrated in U.S. Pat. No. 3,964,474 to Fox. The cervical collar here is made of plastic foam and includes a thin band of resilient plastic material biasing the foam into an annular shape terminating in opposed rear ends which may be separated to circumferentially expand the collar against the bias of the band for fitting about a patient's neck. A front central top portion of the collar includes a depression and the top surface itself is beveled and shaped in such a manner as to comfortably cradle a patient's front jaw portion and side areas of the head. An outer covering of fabric material may be applied about the collar for purposes of cleanliness and enhancement of the aesthetic appearance of the collar. This device is designed to support the user's neck in an upright position and not in a flexion position. It does not and cannot support the head and neck in flexion during downward-looking activities.

Another example of the prior art is illustrated in U.S. Pat. No. 4,232,663 to Newton. The cervical collar here is made of a pad of resilient foam material with a scalloped depressed area at the middle of the inside surface of the collar whereby a user's chin is supported in the depression and pressure on a user's throat area is relieved by the reduced thickness provided by the depression. This collar does not and cannot support the head and neck in flexion during downward-looking activities.

Another example of the prior art is illustrated in U.S. Pat. No. 4,617,691 to Monti et al. This device is a generally rectangular or other suitably shaped support pillow that is adapted to be removably secured around a user's neck. A single elongated wedge-shaped pillow segment is provided with fasteners for joining one end to the other. The wedge shape gives increased lateral support to the user's neck and head. Worn with the fasteners under the user's chin, it gives increased head and neck support whereas if it is worn with the fasteners behind the users head, it gives increased chin and head support. A three-piece version is also provided, and the various pillow segments may be of various sizes. A laminate may be applied to render the support pillow bacteria proof, flame retardant and waterproof while allowing heat and perspiration to escape. A spring-like closure version is also shown. This device is not intended to give support while the user is in a neck flexion position but more to function as a comfortable support for a head and neck to be used while sleeping or resting in a seated or vertical position. As such, this device does not and cannot support the head and neck in flexion during downward-looking activities.

Another example of the prior art is illustrated in U.S. Pat. No. 5,029,577 to Sarkozi. This is a soft neck support collar comprising two offset and attached, tubular ring elements, each element hooking together at their respective ends. Both ring elements contain a soft fill material such as nylon, cotton, polyester, acrylics, foam, foam chips, etc. The combined effect of the fill material together with the tubular configuration, enables the neck to adjust for lateral forward and backward forces during movement. The upper ring element is tapered at each end, so that when these ends are joined together, a space is formed into which the chin can fit, thereby maintaining the neck in a neutral position, and preventing hyperextension. The lower ring element is hooked together at each end, and the rings are offset to enable the lower ring to close at the back of the neck, approximately opposite from the closure of the upper ring element. Hence, the lower ring element functions as a continuous, uniform tubular-shaped ring which does not interfere with movement of the chin. Thus, in the closed configuration, the neck support collar allows for neutral positioning of the chin and neck, and restricts neck mobility. This collar also does not and cannot support the head and neck in flexion during downward-looking activities.

Another example of the prior art is illustrated in U.S. Pat. No. 5,303,890 to Carruth. This device is a chin rest that is arranged to include a housing having a top wall to include a pad member mounted therein. The housing includes first and second leg tubes mounted to opposed ends of the housing, that in turn include first and second respective extension legs that are provided with support pads to position the organization relative to an underlying support surface permitting an individual to rest the chin thereon during reading and other events when the individual is in the supine position, not a standing or seated position. This chin rest does not support or unload the neck of the user while performing activities that require cervical/neck flexion. It does not and cannot support the head and neck in flexion during downward-looking activities.

It is apparent that numerous head supports have been provided in the prior art that are adapted to be used in various contexts. However, even though these innovations may be suitable for the specific individual purposes to which they address, they would not be suitable for the purposes of the present invention as heretofore described.

Accordingly, there is a long-felt need for an adjustable device wearable during any activity that involves any prolonged or short duration cervical flexion that comfortably supports the cervical and upper thoracic spine and related soft tissue components. Such a device must comfortably transfer the load of the head to the cushion and upper chest of the patient and allow the neck muscles to be active when they need to be to rotate or extend the head. Such a device must facilitate a method of unloading the neck and its associated soft tissue and joints. The long sought-after but as yet unrealized device has to be inexpensive to manufacture, easy to use, and completely portable.

SUMMARY OF THE INVENTION

The invention is a spine and neck support device adapted to support the anatomical structures in the cervical and upper thoracic spine when the user's neck is in flexion. The support device includes a cushion adapted to conform about the user's anatomical structures of the neck and rest on the upper chest of the person, the cushion having a chin support area. The cushion and chin support area thereof are dimensioned to avoid contacting the user's chin when the user's head is in a neutral position and dimensioned to contact the user's chin at the chin support area when the user's neck is in flexion. When the user's neck is flexed and the user's chin contacts the chin support area, the cushion unloads and supports the user's neck. Sides of the cushion are preferably rounded for comfort of the user. A superior-most surface of the cushion is preferably sloped downwards from a posterior to anterior direction, wherein the downward slope is adapted to maximize downward field of vision for the user when the user places his chin in the chin support area. The downward slope is preferably at an angle of substantially 45 degrees. Preferably, the material of the cushion provides a progressive resistance to compression.

The chin support area of the cushion preferably further includes an indention located posteriorly and substantially centrally on the superior-most surface. In a preferred embodiment, the chin support area indention measures approximately 2 inches wide and 3 inches long and ½ inch deep.

Several features are provided for the comfort of the user and to accommodate the user's various anatomical structures. For example, a posterior surface of the cushion is concave from side to side so as to minimize interference with the external carotid artery or jugular vein of the user. Additionally, a substantially vertical groove is preferably provided located substantially centrally in the posterior surface, adapted to accommodate the user's trachea and esophagus so as to minimize/eliminate the feeling of choking. In one embodiment, the vertical groove preferably measures approximately 2 inches wide and 0.5-1.0 inches deep. A lower region of the cushion is preferably made concave from side to side to accommodate the upper chest and sternum of the user. Also, a posterior portion of the lower region further includes two clavicular indentions adapted to fit over the clavicular heads of the user. In one embodiment, the clavicular indentions measure approximately 0.5 inches wide, 0.25-0.5 inches deep, and 1.5-2.0 inches apart.

The inventive support device could be used solely with the cushion, using the weight of the user's head when he looks down to trap the cushion between the chin and the chest to maintain the position of the cushion. However, preferably, the invention preferably includes at least one strap attached to the cushion and adapted to secure the cushion to the user. The strap preferably includes a fastener selectively securing the cushion to the user, so that the fastener is closed will hold the cushion in place during use when the user's neck is in a flexed position and also when the user's neck is not in a flexed position. The fastener may include hook and loop fastening sections with one of the hook and loop sections being disposed on the strap and the other of the hook and loop sections being disposed on the cushion, or it may include a quick release buckle. The strap may preferably include two straps, each of the straps being attached to a respective end of the cushion and attachable to the other of the straps behind the user's neck.

The inventive support device will help prevent or minimize cervico-thoracic spine injuries as a result of prolonged positions in cervical/neck flexion and can be used by either a male or female from adolescents to adults. This cervical cushion and therapy device can also be used to help rehabilitate a cervical/neck/thoracic spine that has been injured from the excessive strain and wear and tear from prolonged cervical/thoracic flexion postures. This can help the user return to their prior functional level in a shorter period of time. The anatomical region involved includes the occipital-cervical junction, cervicothoracic junction, cervical vertebrae, the upper thoracic vertebrae and all of the associated muscles, ligaments, tendons and other connective tissues in these regions. This cushion will also allow the user a significant amount of range of motion as there are no restrictions into extension (i.e., one can freely look upwards with one's head tilting back). The user will also be able to freely rotate his head while resting their chin on the cushion as the cushion is not immobile nor does it restrict this movement.

The present invention is directed to a head-and-neck support cushion that can be worn during sitting or standing activities while the user is in a cervical flexion position. This invention provides support for the base of the skull, down the posterior cervical region of the spine, i.e., the neck, and to the upper thoracic region. Suitable activities for the use of this device include, but are not limited to studying, performing prolonged surgeries in the operating room, looking down into a microscope, looking down while working on a computer, reading, working on a patient (e.g., as a dentist might), any manual labor seated and looking down for extended periods of time, and sleeping. The support cushion includes an elongated head and neck foam attached to a harness that includes a main strap. When the head and neck support cushion is placed under the chin in front of the neck, the main strap extends from either end of the neck cushion around the neck and clips together behind the neck. The strap only contacts the neck at the sides and back, eliminating any other points of contact that restrict movement. This end-of-cushion attachment of straps also provides for a backward pull on the cushion, thus allowing adequate support and will keep the cushion in place when the head-and-neck are in a flexed position or if the user is not in a cervical flexion position.

In one embodiment, a nylon strap is sewn on either end of the cushion. One of the nylon straps is threaded into a tensioning connector that allows for tightening and loosening of the cushion. This tensioning connector is attached to one end of the main strap. A buckle attaches the tensioning connector to the other strap. The buckle can be a snap connection and can include an additional tensioner.

In another embodiment, the nylon straps are connected to each other behind the neck by a hook and loop fastener attachment. This will also allow the length of the straps to be adjustable.

The head-and-neck cushion supports the head-and-neck during cervical flexion activities, i.e., head tilted-down activities. The cushion will come in three different sizes to accommodate different size necks and to allow both male and female users, from adolescents to adults, to use it. The cushion is concave posteriorly to conform to the shape of the neck. The cushion has a concave side that is intended to be the surface making contact with the front of the neck. On the superior and proximal surface of the cushion in the middle will be an indention for the chin to rest in. On the posterior portion of the cushion (the portion that contacts the neck) a vertical groove is placed in the middle for the trachea to rest in. The inferior and posterior portion of the cushion will have two indentions for each head of the clavicles as well as a protrusion between these two indentions to fill up the space for the sternal notch. Having the attachment points on the ends of the cushion uniformly and conformingly draws the cushion around the neck when the tensioners or length adjusters in the strap are tightened.

BRIEF DESCRIPTION OF THE DRAWINGS

FIG. 8 is a front elevation view of a user wearing a head and neck support cushion in accordance with the invention with the user's neck in a downward flexed position.

FIG. 9 is a side elevation view of a user wearing a head and neck support cushion in accordance with the invention with the user's neck in a downward flexed position.

DETAILED DESCRIPTION OF THE INVENTION AND DRAWINGS

Description will now be given with reference to the attached FIGS. 1-9. It should be understood that these figures are exemplary in nature and in no way serve to limit the scope of the invention, which is defined by the claims appearing hereinbelow.

As seen in FIGS. 1-5, the head and neck support cushion comprises three basic elements: a base support structure, a covering, and an attachment strap.

The function of the base support structure is to provide a stable platform for transferring the load or weight of the user's head onto the foam, the user's upper sternum/chest, and clavicles while the user is in neck/cervical flexion. By doing this, the load that would normally be placed on the cervical and upper thoracic joints, intervertebral discs, ligaments, tendons, and muscles is transferred to the cushion and the user's anterior upper chest. This will allow the user to maintain a cervical/upper thoracic flexion position for longer periods of time without experiencing pain or strain. A preferred fastening means is a conventional quick release buckle having one end with flexible prongs and another end with receptacles for the flexible prongs. Other known fasteners such as latch assemblies, snaps, cinches, hook and loop fastener, or combinations of these can be used.

Figure 1:
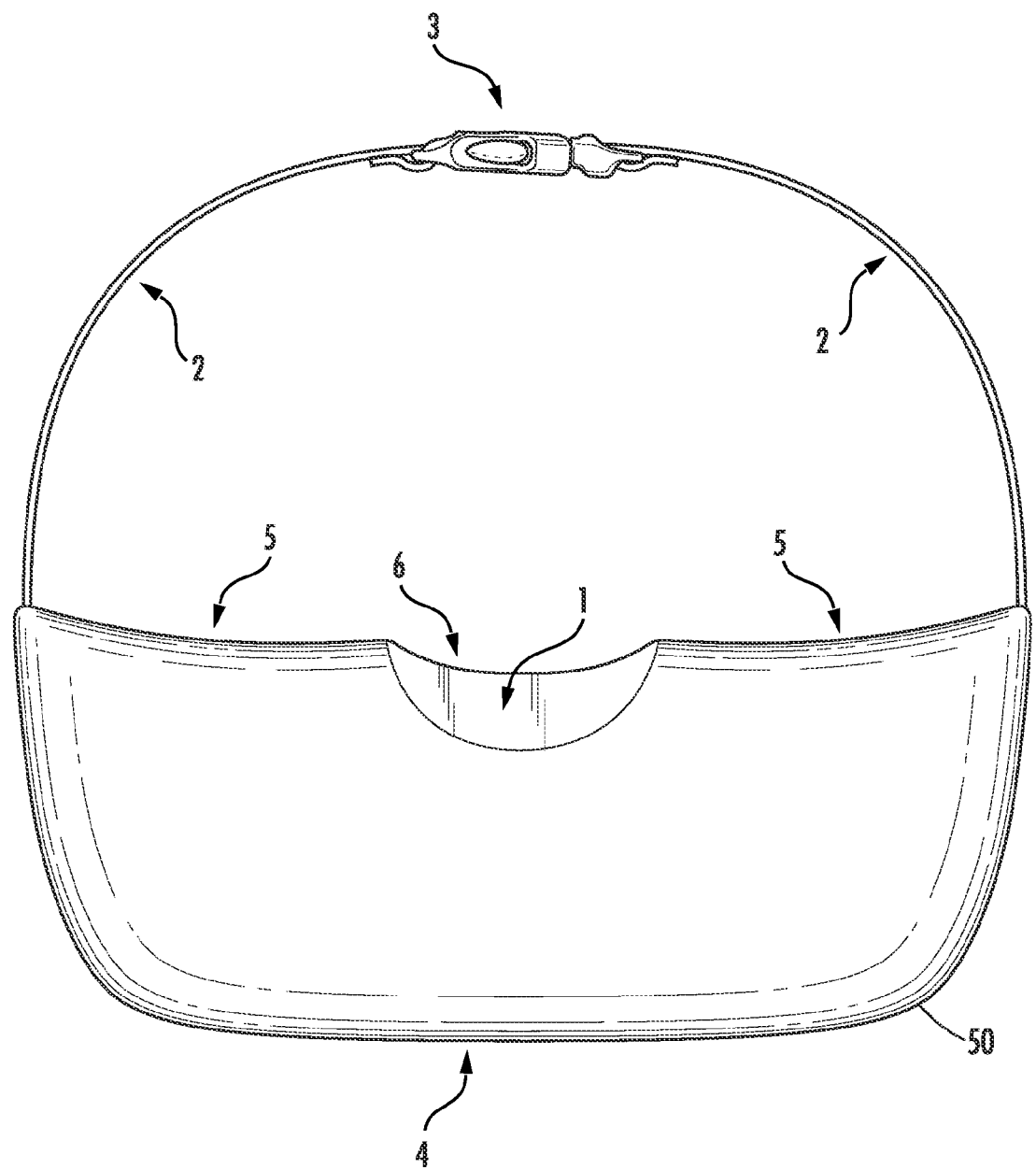
FIG. 1 is a top elevation view of a head and neck support cushion in accordance with the invention.

Referring initially to FIG. 1, an embodiment of a head and neck support device in accordance with the present invention is illustrated. The head-and-neck support device includes an elongated cushion 50, preferably made of foam and having a curved or C-shape. The posterior surface (5) is concave which contacts and conforms to the contours of the anterior neck of the user. The superior surface has an indention (1) (half circle shaped) posterior and on the superior surface (1) which functions as the chin groove or chin rest. This half-circle indention (1) preferably measures approximately 2 inches wide and 3 inches long and ½ inch deep. In the center of the posterior surface lies a groove (6) which functions as the space for the user's trachea. This groove measures approximately 2 inches wide and a depth of 0.5-1.0 inches and is intended to minimize the sensation of something pushing against the user's trachea to minimize the sensation of choking. The anterior portion is convex (4). The dimensions given are appropriate for a cushion designed for an average adult. The dimensions may be larger or smaller for different sizes, or for children's cushions, or for different uses (e.g., a dentist's cushion may be angled or sized differently from a surgeon's cushion).

In one embodiment, the elongated cushion is constructed of one or more cushioning materials surrounded by a fabric cover. The preferred materials for cushion 50 include shape-conforming latex or viscoelastic memory foam and/or polyurethane flexi-foam to provide support, or an open cell foam including or similar to the Omaion® foam developed by Olin Corporation of Clayton, Mo. Other suitable materials for the elongated cushion include styrofoam, rubber, cotton or other cushioning materials. Any suitable fabric can be used including natural and synthetic fabrics as well as fabric that provides for the wicking of moisture away from the skin. Alternatively, the cushion can be one piece molded foam rubber with a protective outer coating.

Referring to FIGS. 1-5, a length of strap (2) is attached to each end and on the posterior portion of the ends of the head-and-neck support cushion. Suitable straps include synthetic or polymer webbings such as nylon webbing. This strap, as well as all other strapping used herein, can have a length of about 6" up to about 10" each with a width of approximately F. The strap is secured to the ends of the head-and-neck support cushion with stitching. In another embodiment, a first part of a two-part quick release mechanism or buckle (3) is attached to each one of the non-stitched ends of the head-and-neck support cushion. Any suitable two-part quick release mechanism can be used. Once each end of the straps is buckled together the head-and-neck support cushion will have a closed circular shape (FIG. 1, FIG. 2, FIG. 3, and FIG. 5). The length of the strap can be adjusted as desired, and this adjustment, since it is pulling backwards on the ends of the neck cushion, conforms the cushion to the front of the user's neck, extending partially to each side of the user's cervical region, i.e., neck. There is no connection between the main strap and the neck cushion in front of the user, and no pads or straps run vertically up the spine between the shoulder blades. This provides a greater degree of unobstructed movement to both the head and arms. The quick release mechanism/buckle is located behind the user on the back of their neck. This placement makes it easy for the user to access and to activate the quick release mechanism/buckle for easy and quick removal of the cushion.

Figure 2:
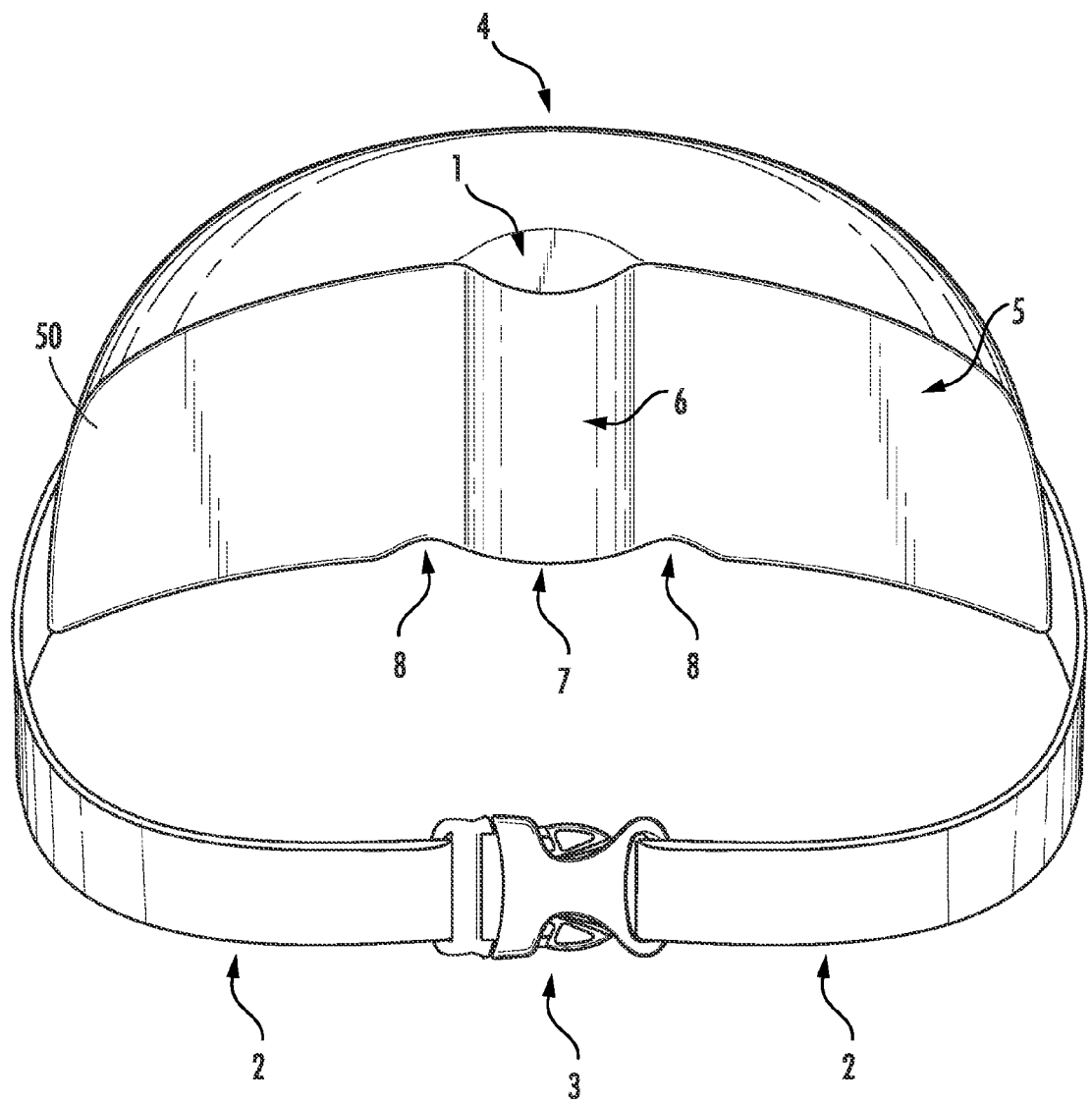
FIG. 2 is a rear perspective view of the head and neck support cushion of FIG. 1.

Referring to FIG. 2, the inferior/posterior portion of the head-and-neck support cushion has two indentions (8), which functions to fit the clavicular heads. Indentions (8) preferably measure approximately 0.5 inches wide, 0.25-0.5 inches deep, and 1.5-2.0 inches apart and are provided for comfort during use. In between indentions (8) is a protrusion (7) which functions to fill in for the sternal notch. This functions to have the head-and-neck support cushion form fitting as much as possible to maximize comfort. FIG. 2 also demonstrates the concave posterior surface (5) and the convex anterior portion (4). As in FIG. 1, running down the center of the posterior portion is the groove (6) for the trachea to fit in as well as the chin indention/rest (1).

Figure 3:
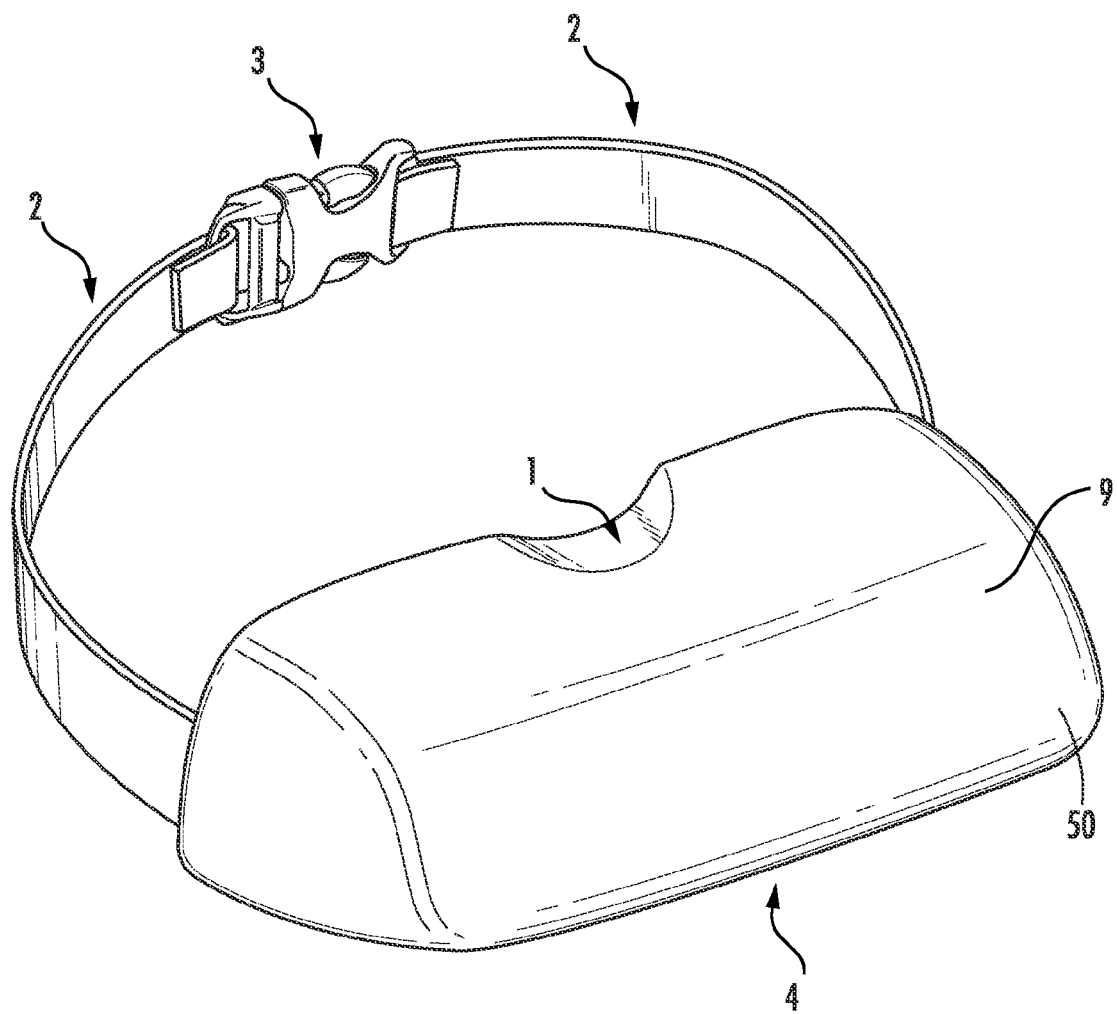
FIG. 3 is an anterolateral perspective view of the head and neck support cushion of FIGS. 1-2.

Referring to FIG. 3, the superior surface has a downward slope of approximately 45 degrees from posterior to anterior (9) to allow greater visibility for the user while performing activities in a cervical flexed position. This figure also illustrates the superior/posterior indention for the chin support (1), the nylon straps attached to the sides (2), and the buckle attaching the straps together (3) and the convex anterior (4).

Figure 4:
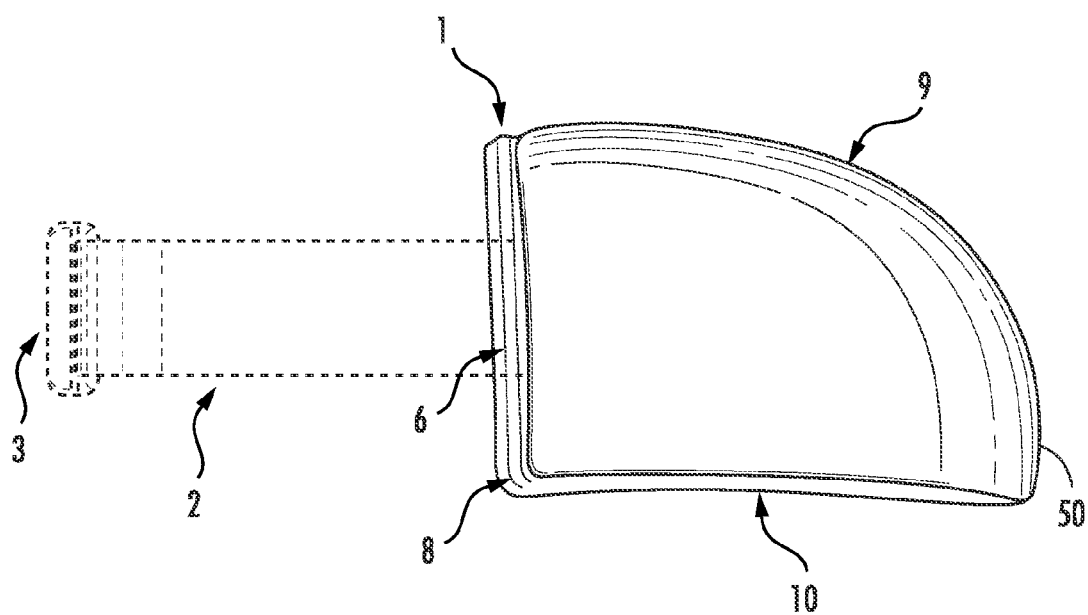
FIG. 4 is side elevation view of the head and neck support cushion of FIGS. 1-3.

Referring to FIG. 4, the inferior surface (10) is concave, which functions to better conform to the natural shape of the sternum/upper chest. The downward slope of the superior surface (9) is also illustrated in this figure. The indention (1) for the chin is not visible in this figure. The groove for the trachea (6) and the two indentions (8), which functions to fit the clavicular heads are also appreciated in this Figure. The straps attached to the sides (2) as well as the hook and loop fastener/buckle is also shown.

Figure 5:
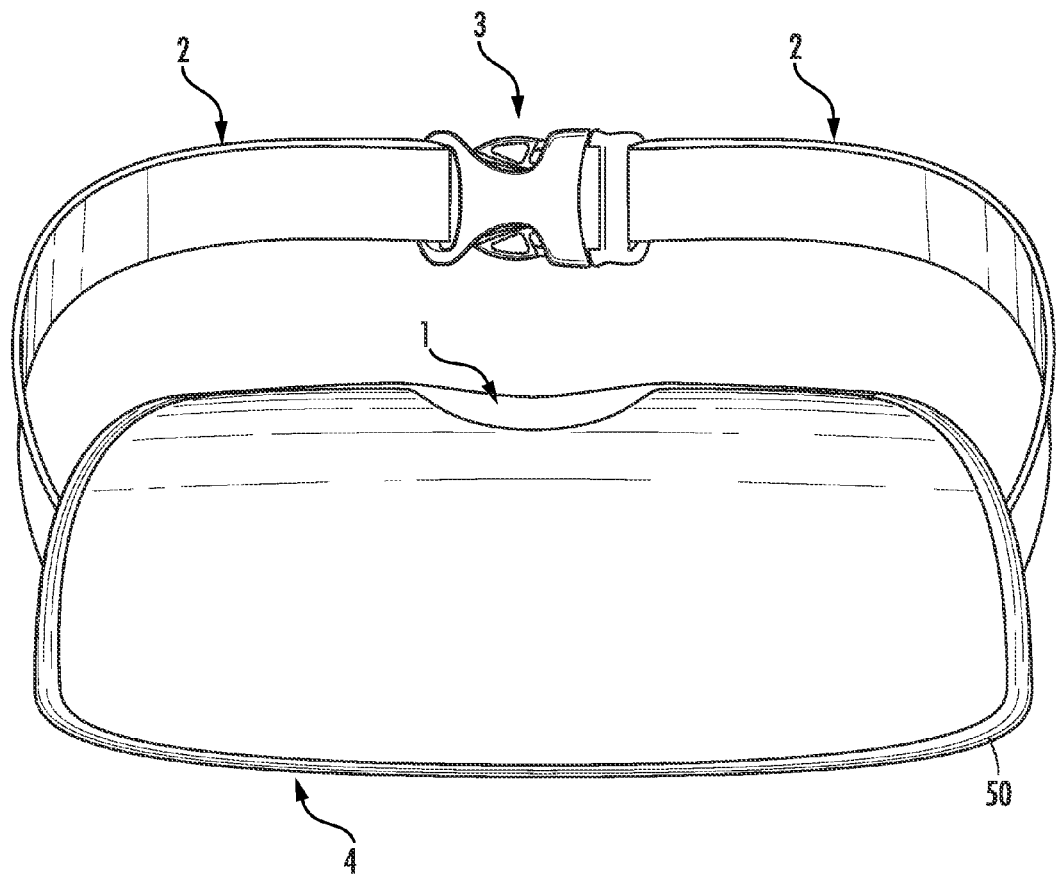
FIG. 5 is an anterolateral perspective view of the head and neck support cushion of FIGS. 1-2.
Figure 6:
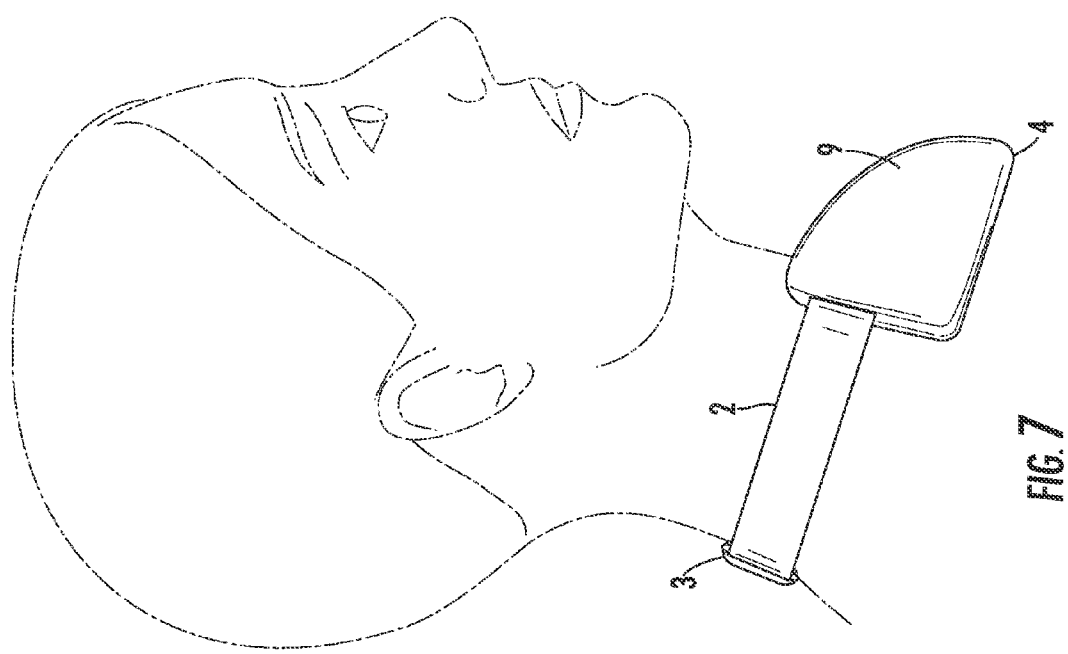
FIG. 6 is a front elevation view of a user wearing a head and neck support cushion in accordance with the invention with the user's head in a neutral position.
Figure 7:
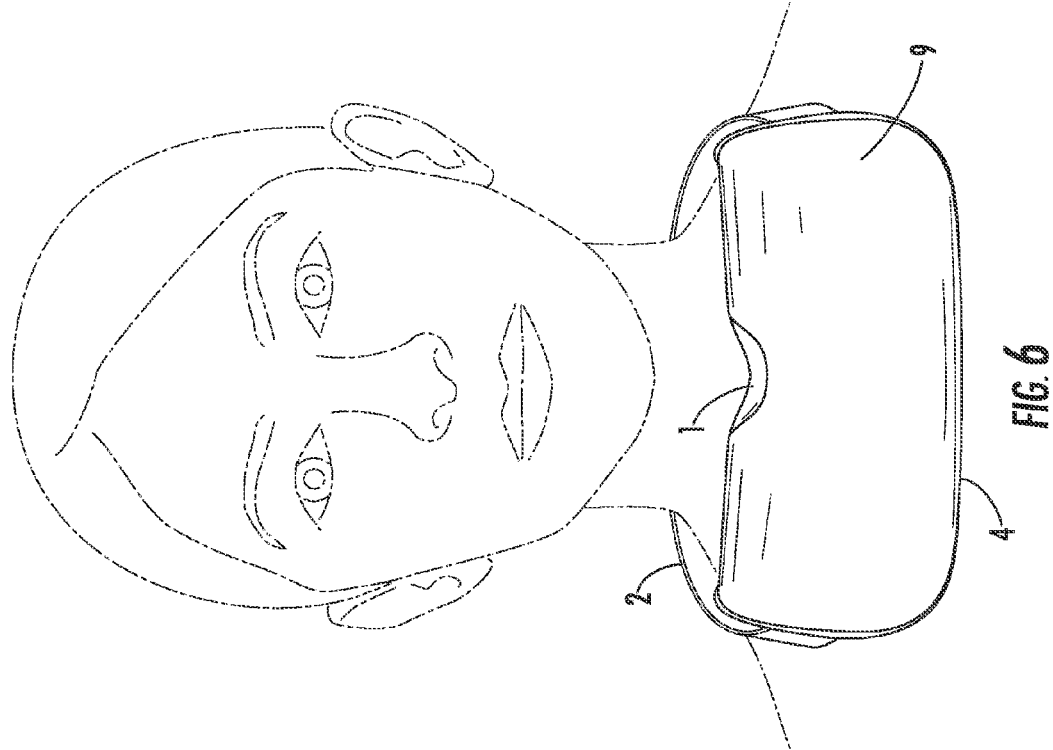
FIG. 7 is a side elevation view of a user wearing a head and neck support cushion in accordance with the invention with the user's head in a neutral position.

Referring to FIG. 5, the anterior view of the head-and-neck support cushion is depicted from a slightly superior angle to depict the indention for the chin rest (1). The convex anterior portion is seen in this figure. The straps (2) attaching to buckle (3) are seen in this figure.

Thus, the present invention fulfills the need of facilitating a method of cervical/neck support where the load of the head is transferred to the upper chest and cushion and the head and neck can actively rotate in progressively flexion ranges of motion while allowing the user to extend their neck without any restrictions. As best illustrated in FIGS. 6-9, the user is wholly free to move his head up, down, and laterally without restriction from the inventive cushion (see FIGS. 6 and 7). When the user flexes his neck downward (see FIGS. 8 and 9), the user's chin engages chin indention (1) and can rest comfortably there, rather than being held above the user's chest and placing an uncomfortable load on the posterior neck muscles, the cervical spine, and related anatomical structures.

The present invention can be easily donned and removed. To don the head and neck support cushion, the user will grab the unconnected straps (2) in each hand, making sure the chin indention (1) is facing upwards. The user will then bring the head and neck support cushion underneath their chin until it makes contact with their anterior neck. The user will then connect the two straps (2) behind their neck by inserting one end of the strap into the other to complete the buckle (3). This is performed while the user is looking forward with their neck/cervical spine in a neutral position. The length of the straps can be adjusted at the buckle (3) to make sure the head and neck support cushion is properly in place resting against the user's anterior neck and the user's chin is in contact with the chin indention (1) when the user looks down (flexes their neck). The head and neck support cushion is removed by simply reaching around and releasing the buckle (3). Of course, the straps need not be both the same length, and indeed, only one strap may be provided fixed at one end to one side of cushion (50) and attachable at the other end to the opposite side of cushion (50), either by a hook and loop fastening system, by a quick release buckle, or the like.

Having described certain embodiments of the invention, it should be understood that the invention is not limited to the above description or the attached exemplary drawings.

Rather, the scope of the invention is defined by the claims appearing hereinbelow and any equivalents thereof as would be appreciated by one of ordinary skill in the art.

What is claimed is:

1. A spine and neck support device adapted to support the anatomical structures in the cervical and upper thoracic spine when the user's head is tilted downwardly at about 45° and the neck is in flexion, comprising: a cushion adapted to conform about the user's anatomical structures of the neck and rest against and up on the upper chest of the person, said cushion having a chin support area, said cushion having a thickness dimensioned to avoid contacting the user's chin when the user's head is in a neutral, non-tilting position, and dimensioned to contact the user's chin at said chin support area when the user's neck is in flexion with the head at a downward tilt of about 45°, wherein when the user's neck is flexed and the user's chin contacts said chin support area, said cushion unloads and supports said user's neck and prevents said user's neck from direct contact with the user's upper chest, said cushion having a superiormost surface substantially sloped convexly downwardly at an angle of substantially 45 degrees from a posterior to anterior direction, wherein said superiormost surface is adapted to maximize and allow downward field of vision for the user when the user places said chin in said chin support area.

2. A spine and neck support device according to claim 1, wherein sides of said cushion are rounded for comfort of the user.

3. A spine and neck support device according to claim 1, said chin support area further comprising an indention located posteriorly and substantially centrally on the superior-most surface.

4. A spine and neck support device according to claim 3, said chin support area indention measuring approximately 2 inches wide and 3 inches long and ½ inch deep.

5. A spine and neck support device according to claim 1, wherein a posterior surface of said cushion is concave from side to side, adapted to minimize interference with the external carotid artery or jugular vein of the user.

6. A spine and neck support device according to claim 1, further comprising a substantially vertical groove located substantially centrally in said posterior surface, adapted to accommodate the user's trachea and esophagus.

7. A spine and neck support device according to claim 6, said vertical groove measuring approximately 2 inches wide and 0.5-1.0 inches deep.

8. A spine and neck support device according to claim 6, wherein a lower region of said cushion is concave from side to side to accommodate the upper chest and sternum of the user.

9. A spine and neck support device according to claim 8, wherein a posterior portion of said lower region further comprises two clavicular indentions adapted to fit over clavicular heads of the user.

10. A spine and neck support device according to claim 9, wherein said clavicular indentions measure approximately 0.5 inches wide, 0.25-0.5 inches deep, and 1.5-2.0 inches apart.

11. A spine and neck support device according to claim 1, further comprising at least one strap attached to said cushion and adapted to secure said cushion to the user.

12. A spine and neck support device according to claim 11, said strap further comprising a fastener selectively securing said cushion to the user, wherein when said fastener is closed will hold said cushion in place during use when the user's neck is in a flexed position and also when the user's neck is not in a flexed position.

13. A spine and neck support device according to claim 12, said fastener including hook and loop fastening sections with one of said hook and loop sections being disposed on said strap and the other of said hook and loop sections being disposed on said cushion.

14. A spine and neck support device according to claim 12, wherein said at least one strap further comprises two straps, each of said straps being attached to a respective end of said cushion and attachable to the other of said straps behind the user's neck.

15. A spine and neck support device according to claim 14, wherein said straps are attachable together via a quick release buckle.

16. A spine and neck support device according to claim 14, wherein said straps are attachable together via hook and loop fastening sections.

17. A spine and neck support device according to claim 11, wherein one end of said strap is attached to said cushion and the other end of said strap is attachable to said cushion via a quick release buckle.

18. A spine and neck support device according to claim 1, wherein the material of said cushion provides a progressive resistance to compression.

* * * * *